United States Patent
Niznick

(10) Patent No.: US 7,014,464 B2
(45) Date of Patent: Mar. 21, 2006

(54) MULTI-PART ABUTMENT AND TRANSFER CAP FOR USE WITH AN ENDOSSEOUS DENTAL IMPLANT WITH NON-CIRCULAR, BEVELED IMPLANT/ABUTMENT INTERFACE

(76) Inventor: Gerald A. Niznick, 3993 Howard Hughes Pkwy., #540, Las Vegas, NV (US) 89109

( * ) Notice: Subject to any disclaimer, the term of this patent is extended or adjusted under 35 U.S.C. 154(b) by 0 days.

(21) Appl. No.: 10/741,023

(22) Filed: Dec. 19, 2003

(65) Prior Publication Data

US 2005/0136379 A1    Jun. 23, 2005

(51) Int. Cl.
*A61C 8/00* (2006.01)
(52) U.S. Cl. ............................ 433/173; 433/174
(58) Field of Classification Search ............... 433/173, 433/174
See application file for complete search history.

(56) References Cited

U.S. PATENT DOCUMENTS

| | | | | |
|---|---|---|---|---|
| 5,195,892 A | * | 3/1993 | Gersberg | 433/174 |
| 5,246,370 A | * | 9/1993 | Coatoam | 433/173 |
| 5,302,126 A | | 4/1994 | Wimmer et al. | |
| 5,334,024 A | * | 8/1994 | Niznick | 433/173 |
| 5,527,183 A | * | 6/1996 | O'Brien | 433/174 |
| 5,564,923 A | * | 10/1996 | Grassi et al. | 433/173 |
| 5,688,123 A | * | 11/1997 | Meiers et al. | 433/173 |
| 5,782,918 A | * | 7/1998 | Klardie et al. | 606/60 |
| 5,810,592 A | * | 9/1998 | Daftary | 433/173 |
| 5,823,776 A | * | 10/1998 | Duerr et al. | 433/173 |
| 6,116,904 A | | 9/2000 | Kirsch et al. | |
| 6,168,436 B1 | * | 1/2001 | O'Brien | 433/173 |
| 6,227,859 B1 | | 5/2001 | Sutter | |
| 6,431,866 B1 | * | 8/2002 | Hurson | 433/172 |
| 6,648,643 B1 | | 11/2003 | Hollander et al. | |
| 6,659,770 B1 | * | 12/2003 | Crudo | 433/173 |

* cited by examiner

Primary Examiner—Ralph A. Lewis
(74) Attorney, Agent, or Firm—Patrick F. Bright

(57) ABSTRACT

A multi-part abutment for use with an endosseous dental implant includes a first part with a tapered portion at its proximal end adapted to accept a dental restoration and an optional transfer cap, a distally-positioned external multi-lobed or other wrench-engaging portion, an inwardly-projecting non-circular bevel extending partly or entirely around the first part, connecting the proximal and wrench-engaging portions. The first part has an internal through passage with an internal projection or threads or both. The second abutment part, a screw, has a proximal region to engage the internal projection(s) or threads or both of the first part, and a threaded shank to engage internal threads in an endosseous dental implant.

9 Claims, 2 Drawing Sheets

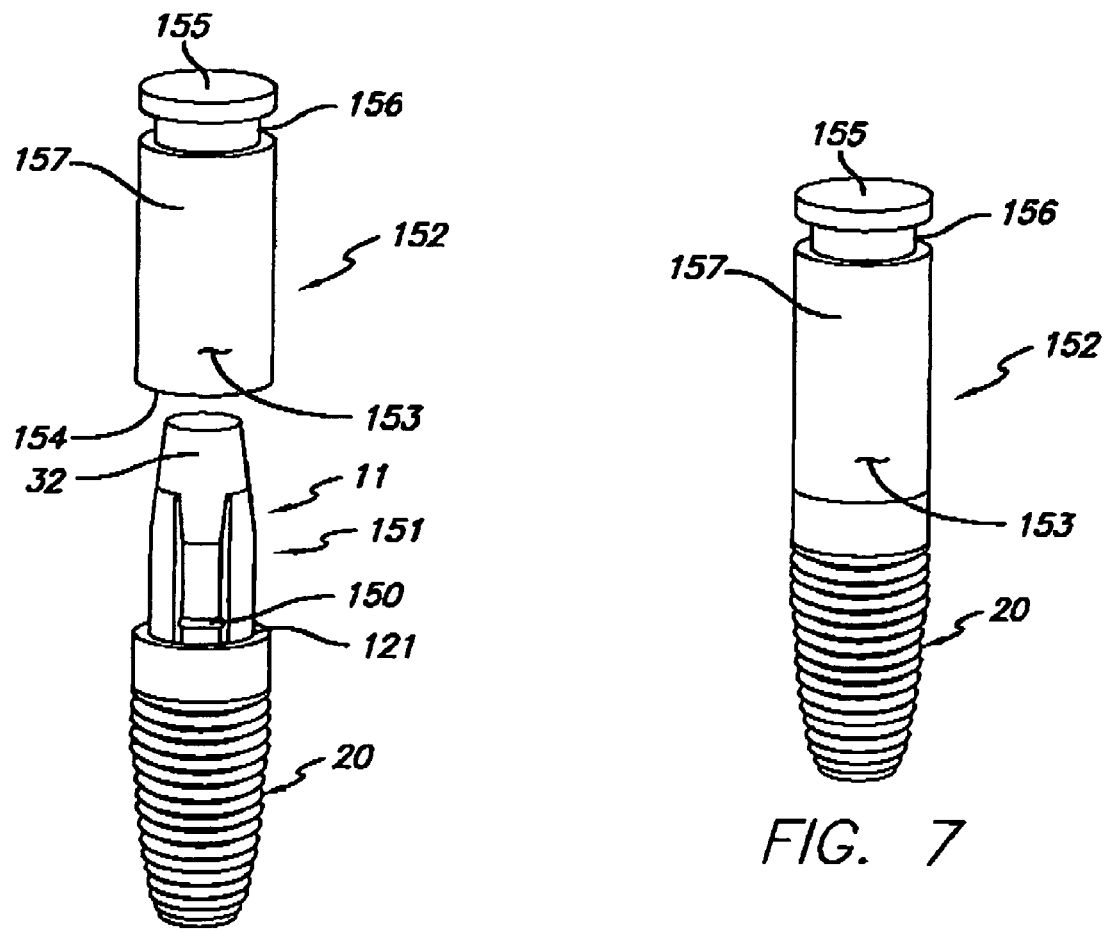
FIG. 6
FIG. 7
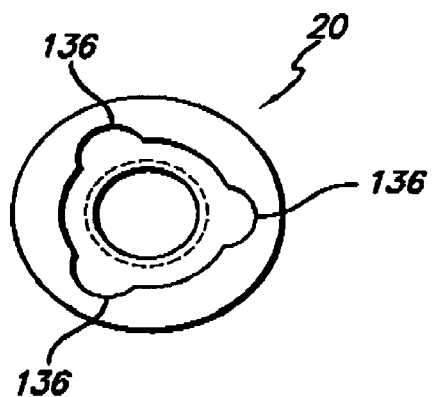
FIG. 8 ed shaft, or a healing collar can be attached to the implant from the time the implant is placed until the final restoration is ready.

MULTI-PART ABUTMENT AND TRANSFER CAP FOR USE WITH AN ENDOSSEOUS DENTAL IMPLANT WITH NON-CIRCULAR, BEVELED IMPLANT/ABUTMENT INTERFACE

This invention relates to multi-part abutments for endosseous dental implants, and more particularly, to abutments for use with implants that comprise a body portion having a top surface, and a beveled non-circular opening at the top surface. This opening leads into a closed-ended, internally-threaded shaft or passage in the implant that includes a lead-in, non-circular bevel, formed entirely or partly around the opening; female, wrench-engaging surfaces inside this shaft or passage; and an internally-threaded portion, distal to the wrench-engaging surfaces. In some embodiments, the wrench-engaging surfaces comprise three or more slots as shown, for example, in Kirsch U.S. Pat. No. 6,116,904, issued Sep. 12, 2000, and entitled "Endosteal Single Tooth Implant Secured Against Torsion, Stamping Tool and Positioning Aid For Producing Such A Single Tooth Implant", or one or more points as shown, for example, in U.S. Pat. No. 4,960,381, issued Oct. 2, 1990, and entitled "Screw-Type Dental Implant Anchor". The entire disclosures of the '904 and '381 patents are incorporated herein by this reference.

These multi-part abutments, in preferred embodiments, comprise two parts. The first part engages both the female, preferably multi-lobed, more preferably tri-lobed, internal, wrench-engaging surfaces of the implant, and the non-circular bevel that partly or completely surrounds the top part of the internally-threaded shaft of the implant. Preferably, this first part extends radially to, but not beyond, the non-circular bevel at the opening to the internal shaft of an implant, leaving the top surface of the implant peripheral to the bevel exposed, thus providing adequate surface for seating of a cemented restoration. The first part also comprises a longitudinal, internal, through passage that preferably includes internal threads and/or an internal flange at or near the central portion of the through passage. The threads and/or flange serve to retain a fixation screw that passes through the internal passage of the abutment.

In preferred embodiments, the first part comprises, at its proximal end, a tapered portion adapted to engage a cemented dental restoration with a non-circular interface for anti-rotational stability. In some embodiments, the outer surface of the tapered portion may include a plurality of grooves, notches, or other inwardly-projecting indentations.

Connected to, contiguous with, and distal from the tapered portion, in some embodiments, is an external, multi-lobed, preferably tri-lobed, male portion of length and shape complementary to the multi-lobed, female, wrench-engaging surfaces internal to the implant. Preferably, these lobes are spaced substantially equidistant from one another. Other embodiments may instead include multi-sided male portions that engage complementary female wrench-engaging surfaces internal to the implant.

Connected to, contiguous with, and distal from this multi-lobed or multi-sided male portion may be a substantially cylindrical portion that has a size and shape that fits inside the internally-threaded shaft of the implant. When properly seated in the implant, this cylindrical portion is longitudinally separated from the proximal end of the threaded region or area inside the internally-threaded shaft, and that lies below the internal, multi-lobed, female, wrench-engaging surfaces in the internally-threaded shaft. Alternatively, the multi-lobed or multi-sided wrench-engaging surfaces in the internally-threaded shaft of the implant can extend distally to the start of the threaded portion, eliminating the cylindrical portion and the need for a corresponding portion in the distal end of the abutment.

The second part of the two-part abutment is a fixation screw. In preferred embodiments, this screw has a distal, threaded shank portion, an unthreaded middle portion connected at one end to the shank portion, and a proximal portion connected at the other end to the unthreaded middle portion. The proximal portion comprises a tool-engaging, preferably wrench-engaging, structure to receive a tool for inserting the second part into the internal passage of the first part, and for screwing the second part of the abutment through the internal structure inside of the first part of the abutment, and then into engagement with the internal structure in the internally-threaded shaft of the implant, thus securing the first and second parts of the abutment to the implant.

The transfer cap of this invention is, in preferred embodiments, a hollow tube closed at the proximal end and open at the distal end, preferably having a cylindrical profile. At or near the closed proximal end of this cap is an undercut region, which, in preferred embodiments, comprises one or more circumferential grooves, or a plurality of openings spaced apart from one another. The distal end of the cap is open to an internal passage that includes, on the inside wall surface, near the opening, one or more retention projections that snap/fit into inwardly-projecting grooves/notches/indentations on the outer surface of the tapered proximal portion of an abutment. Such grooves/notches/indentations may appear on the abutments of this invention, or on another abutment that includes such external, inwardly-projecting indentations on the external surface of the abutment between its proximal end and a wider region of the external surface.

In preferred embodiments, the retention projections on the wall of the inner surface of the transfer cap comprise one or more said projections, complementary in size and shape to the inwardly-projecting grooves/notches/indentations on the outer surface of the tapered portion of an abutment.

In use, after an abutment has been attached to an endosseous dental implant, the transfer cap is placed over an abutment's exposed, tapered proximal abutment portion. The internal projection or projections fit or snap into one or more of the externally-formed grooves, notches or other inwardly-projecting indentations on the outer surface of the tapered portion of the abutment. When so placed, the bottom of the transfer cap preferably seats on the upper exposed surface of the implant.

A dental professional can then use the transfer cap to form a full mouth transfer impression. When impression material placed in a patient's mouth sets, the material locks into the external undercut region near the top of the transfer cap with greater force than the forces holding the transfer cap to the abutment. Removal of the transfer impression material also removes the plastic transfer cap from the abutment. A metal, e.g., titanium, stainless steel or aluminum, abutment replica that duplicates the exposed top surface or shoulder of the implant, the tapered surface of the abutment and the retentive notches/grooves/indentations on the abutment is inserted into the transfer cap held within the impression.

A stone cast is formed by pouring stone material into the impression negative, and around the abutment/implant shoulder replica, to form a working cast upon which a prosthesis can be formed. The abutment that was attached to the implant may be left in place to support a temporary restoration until the final restoration is formed, or the abutment may be removed from the implant, and a healing collar attached to the implant to seal its internally-threaded shaft. The implant/healing cap may be submerged beneath gum tissue for a healing period, or may be left exposed for a non-submerged healing period.

The transfer cap may be made of a suitable plastic, preferably a thermoplastic such as polypropylene, and has sufficient length and width to fit over the tapered proximal portion of an abutment. The cap may be converted to a coping for use in fabrication of a pattern for metal cast superstructure to support porcelain fused to metal restorations or for a gold crown. This is done by removing the undercut at or near the proximal end of the transfer cap, and by removing the projections inside the transfer cap. Alternatively, a second plastic coping, sleeve or tube, that has neither the retentive elements at the top or inside the coping, can replace the transfer cap after a transfer impression is formed for use in fabrication of a metal casting for a restoration.

BRIEF DESCRIPTION OF THE DRAWINGS

This invention can be better understood by reference to the drawings in which:

FIG. 6 is a perspective view of the abutment implant assembly shown in FIG. 2, together with a preferred embodiment of the transfer cap of this invention;

FIG. 7 is a perspective view of the abutment/implant assembly of FIG. 6 with the transfer cap covering the tapered proximal portion of the abutment; and FIG. 8 is a top plan view of the tri-lobed wrench-engaging surfaces of the implant shown in FIGS. 1 through 7.

DETAILED DESCRIPTION OF THE DRAWINGS

Figure 1:
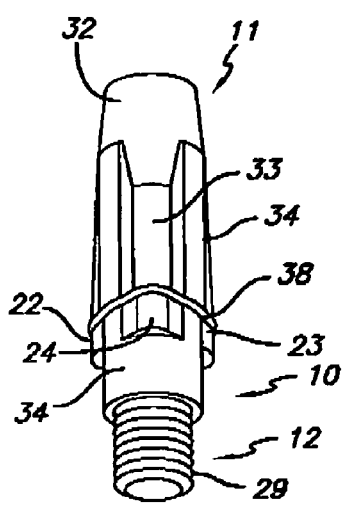
FIG. 1 is a perspective view of a preferred embodiment of the multi-part abutment of this invention.

Referring to the drawings, FIGS. 1–5, and 8, two-part abutment 10 includes first abutment part 11 and second abutment part 12. Second abutment part 12 includes, at its distal end, externally-threaded shank portion 29, and at its proximal end, cylindrical portion 30A with internal insertion tool-engaging passage 30. At the junction of portions 30A and 40 is flange 25. Connecting these two portions is externally-unthreaded cylindrical middle portion 40. Passage 30 may be multi-sided to engage a multi-sided tool, such as an Allen wrench, for threading part 12 into place inside first abutment part 11.

First abutment part 11 includes internally-threaded through passage 28. Passage 28 extends entirely through first abutment part 11. Inside passage 28, near its mid-point, is internally-threaded region 31. When second abutment part 12 is inserted into internal passage 28 in first abutment part 11, distal, externally-threaded portion 29 threads through internally-threaded region 31, which serves to prevent second abutment part 12 from falling out of, or being withdrawn from, internal passage 28 in first abutment part 11.

At the proximal end of first abutment part 11 is prosthesis-engaging portion 32. Portion 32 is frusto-conical and non-circular in shape, and includes three longitudinally-extending, radial protrusions such as protrusions 33 and 34, spaced from one another approximately 120°.

Connected to and contiguous with portion 32 is portion 35, which has three longitudinally-extending, radially-projecting male lobes 22, 23, and 24; such protrusions may serve as external wrench-engaging portions.

First abutment part 11 also includes external non-circular bevel or chamfer 38 that lies between portions 32 and 35, and extends downwardly and inwardly from abutment portion 32 to abutment portion 35. Chamfer 38 is complementary in size and shape to internal, non-circular bevel/chamfer 113 that extends around the opening into passage 130, and also extends downwardly and inwardly from upper flat surface 121 of abutment 20, toward its internally-threaded passage 130.

In use, first abutment part 11 is inserted into implant 20, with male tri-lobed portion 35 seating in female, tri-lobed wrench-engaging surfaces inside internally-threaded passage 130 of implant 20. External, non-circular bevel or chamfer 38 seats in non-circular bevel or chamfer 113. Second implant part 12 is then inserted into internal passage 28 in first abutment part 11. Externally-threaded distal portion 29 of second abutment part 12 threads through internal threads 31 in first abutment part 11, and then threads into internally-threaded region 129 inside implant 20, bringing flange 25 into engagement with the surface of internally-threaded region 31. When so placed inside first abutment part 11, second abutment part 12 holds first abutment part 11 firmly in implant 20. Tri-lobed male portion 35 of first abutment part 11 prevents rotation of abutment 10 with respect to implant 20.

Implant 20 is configured to receive and support one or more dental attachments or components such as, for example, the multi-part abutments of this invention, healing caps, impression copings, and temporary abutments. Implant 20 is preferably made of a dental grade titanium alloy, although other suitable materials can be used.

Figure 2:
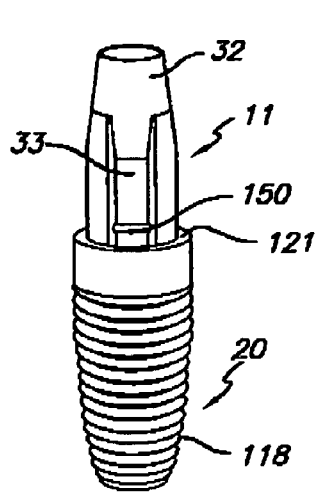
FIG. 2 is a perspective view of the multi-part abutment of FIG. 1, with the addition of external, retentive grooves/notches/indentations, inserted into and affixed to an endosseous dental implant that includes internal, tri-lobed, female wrench-engaging surfaces.
Figure 3:
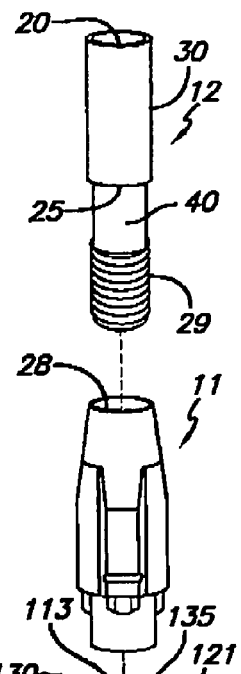
FIG. 3 is a perspective view of the two parts of the abutment and the implant of the abutment/implant assembly of FIG. 2.
Figure 4:
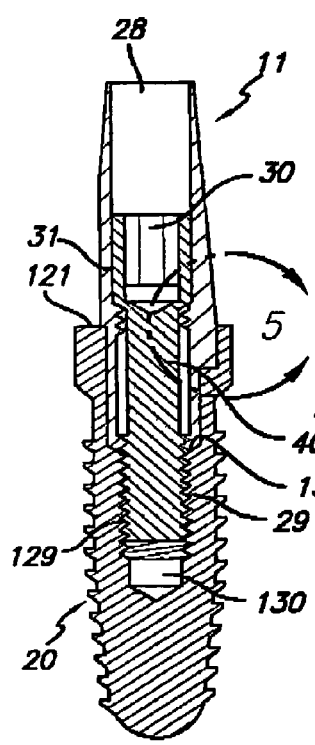
FIG. 4 is an elevation view in cross-section of the implant/abutment assembly of FIGS. 1 and 2.
Figure 5:
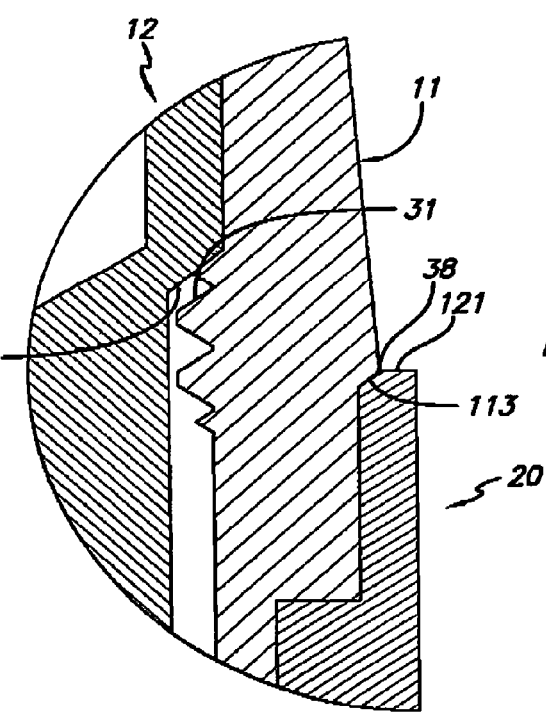
FIG. 5 is an exploded detail view of the circled portion marked—5—in FIG. 4.

As FIGS. 2, 3, and 4 show, the outer surface of implant 20 bears external threads 118. Implant 20 includes an internally-threaded shaft or passage 130 and tri-lobed wrench-engaging region 135. Region 135 includes three semi-circular channels 136. Channels 136 are located approximately 120 degrees apart from each other.

FIGS. 6 and 7 show transfer cap 152 positioned over the proximal end 32 of first abutment part 11, with abutment part 11 seated in implant 20 (see FIG. 2). Transfer cap 152 has a right cylindrical body portion 157 including closed, flat, proximal end 155 and upper, external retention structure 156. Retention structure 156 is a circumferential groove formed just below top surface 155. Transfer cap 152 is open at end 154. Inside transfer cap 152 is a hollow passage.

Transfer cap 152 is a sufficient length and diameter to fit over proximal end 32 of abutment part 11 when the distal surface around opening 154 is seated on upper surface 121 of abutment 20. On the inner surface of transfer cap 152, near opening 154, is a plurality of projections or protrusions 153. These protrusions are of a size and shape complementary to inward projections such as projection 150 on abutment part 11.

FIG. 7 shows transfer cap 152 in place, atop implant 20 with inward projection 153 seated in groove or notch 150, and the dental surface around opening 154 seated on upper surface 121 of abutment 20.

What is claimed is:

1. A multi-part abutment for use with an endosseous dental implant that includes an internal passage with a bevel with a transverse cross-section of approximately circular shape including a plurality of recesses at or near the opening of the passage, and internal threads and internal wrench-engaging surfaces in said passage, comprising:
   a first part comprising a proximal, prosthesis-engaging portion, connected to and contiguous with a portion having an approximately cylindrical shape, said portion including a plurality of distal, external, longitudinally-projecting, male lobes or points or slots;
   said prosthesis-engaging portion and said plurality of male lobes or points or slots being connected by a bevel with a transverse cross-section of approximately circular shape punctuated by one or more projections that extends entirely or partly around said first abutment part, and is of a size and shape to seat in said bevel at or near the opening of the internal passage of said implant;
   said first abutment part further comprising an internal, longitudinal, through passage including an inwardly-projecting surface; and
   a second part comprising a fixation screw having a size and shape to fit into said internal, longitudinal, through passage of said first abutment part, and to engage threads inside said implant, and said inwardly-projecting surface, to hold said abutment in place in said implant.

2. The multi-part abutment of claim 1, wherein said distal plurality of male lobes or sides or points or slots include at least three lobes spaced equidistantly from one another, or is a plurality of points or slots and includes at least three points or slots.

3. The multi-part abutment of claim 1, wherein said first part includes multiple external lobes located in alignment with the plurality of male lobes.

4. The multi-part abutment of claim 1 wherein said plurality of male lobes or points or slots are smaller in diameter than said prosthesis-engaging portion and wherein said cylindrical portion has a smaller diameter than said plurality of male lobes or sides or points or slots.

5. The multi-part abutment of claim 1 wherein said second abutment part comprises a distal, threaded shank portion, and a proximal portion that includes a tool-engaging structure to receive a tool for inserting said second abutment part into said first abutment part.

6. The multi-part abutment of claim 1 wherein said internal projection comprises threads, a flange or both.

7. The multi-part abutment of claim 1 wherein said abutment includes a plurality of male lobes, and said prosthesis-engaging portion includes multiple external protrusions, each aligned with a lobe of said plurality of male lobes.

8. A multi-part abutment for use with an endosseous dental implant includes an internal passage with a bevel with a transverse cross-section of approximately circular shape including a plurality of recesses at or near the opening of the passage, and internal threads and internal wrench-engaging surfaces in said passage, comprising:
   a first part comprising a proximal, prosthesis-engaging portion, connected to and contiguous with a portion having an approximately cylindrical shape, said portion including a plurality of distal, longitudinally-extending, male lobes or sides or points or slots;
   said prosthesis-engaging portion and said plurality of distal, longitudinally-extending male lobes or points or slots being connected by a bevel with a transverse cross-section of approximately circular shape punctuated by one or more projections that extends entirely or partly around said first abutment part, and is of a size and shape to seat in said bevel at or near the opening of the internal passage of said implant;
   said first abutment part further comprising an internal longitudinal through passage with internal projections or threads or both; and
   a second part comprising a fixation screw having a size and shape to fit into said internal longitudinal through passage of said first abutment part, and to engage said internal projections or threads or both inside said implant to hold said abutment in place in said implant.

9. The multi-part abutment of claim 8 wherein said prosthesis-engaging portion includes multiple external protrusions, each aligned with a lobe of said plurality of male lobes.

* * * * *